(12) United States Patent
Tada et al.

(10) Patent No.: US 7,816,549 B2
(45) Date of Patent: Oct. 19, 2010

(54) METAL-CONTAINING COMPOUND, ITS PRODUCTION METHOD, METAL-CONTAINING THIN FILM, AND ITS FORMATION METHOD

(75) Inventors: Ken-ichi Tada, Fujisawa (JP); Koichiro Inaba, Shunan (JP); Taishi Furukawa, Ayase (JP); Tetsu Yamakawa, Tokyo (JP); Noriaki Oshima, Yokohama (JP)

(73) Assignees: Tosoh Corporation, Shunan-Shi (JP); Sagami Chemical Research Center, Ayase-Shi (JP)

( * ) Notice: Subject to any disclaimer, the term of this patent is extended or adjusted under 35 U.S.C. 154(b) by 440 days.

(21) Appl. No.: 11/997,819

(22) PCT Filed: Jul. 28, 2006

(86) PCT No.: PCT/JP2006/315037

§ 371 (c)(1),
(2), (4) Date: Feb. 4, 2008

(87) PCT Pub. No.: WO2007/015436

PCT Pub. Date: Feb. 8, 2007

(65) Prior Publication Data

US 2010/0105936 A1    Apr. 29, 2010

(30) Foreign Application Priority Data

Aug. 4, 2005   (JP) ............... 2005-226886
Nov. 11, 2005  (JP) ............... 2005-326883
Nov. 11, 2005  (JP) ............... 2005-326884

(51) Int. Cl.
*C07F 7/00* (2006.01)
*C07F 5/06* (2006.01)
*C23C 16/00* (2006.01)

(52) U.S. Cl. ............... 556/51; 556/1; 556/176; 427/250; 427/255.19

(58) Field of Classification Search ............... 556/1, 556/51, 176; 427/250, 255.19
See application file for complete search history.

(56) References Cited

U.S. PATENT DOCUMENTS 5,208,187 A     5/1993   Tsubouchi et al.
7,196,211 B2 *  3/2007   Itsuki et al. ............... 556/51
2006/0035462 A1 2/2006   Millward

FOREIGN PATENT DOCUMENTS

CN    1060558 A       4/1992
JP    2003-137551 A   5/2003
JP    2004-196618 A   7/2004

OTHER PUBLICATIONS

Carlmart, Claire J. et al., Synthesis of Titanium (IV) Gaunidinate Complexes and the Formation of Titanium Carbonitride via Low-Pressure Chemical Vapor Deposition, Inorganic Chemistry, 2005, 44(3), pp. 615 to 619.
Kenney, Amanda P. et al., The Insertion of Carbodiimides into Al and Ga Amido Linkages. Guanidinates and Mixed Amino Guanidinates of Aluminum and Gallium, Inorganic Chemistry, 2005, 44 (8), pp. 2926 to 2933.
Dennis M. Hausmann et al. Chemistry of Material. Atomic Layer Deposition of Hafnium and Zirconium Oxides Using Metal Amide Precursors . Harvard University Chemical Laboratories, Cambridge, Massachusetts 02138. 2002 American Chemical Society published Sep. 21, 2002, 14, pp. 4350-4358.
Ju Youn Kim et al. Journal of the Electrochemical SocietyCharacteristics and Compositional Variation of TiN Films Deposited by Remote PEALD on Contact Holes. Department of Materials Science and Engineering, Hangyang University, Seoul 133-791, Korea, 2005, 152(1), pfs. 29-34.
Anthony C. Jones et al. Some recent developments in the MOCVD and ALD of high- dielectric oxides. Journal of Materials Chemistry, 2004, 14, The Royal Society of Chemistry, pp. 3101-3112.
Chinese Office Action issued Apr. 13, 2010 in Chinese application No. 200680029033.2.

* cited by examiner

*Primary Examiner*—Porfirio Nazario Gonzalez
(74) *Attorney, Agent, or Firm*—Sughrue Mion, PLLC

(57) ABSTRACT

A compound which has thermal stability and moderate vaporizability and is satisfactory as a material for the CVD or ALD method; a process for producing the compound; a thin film formed from the compound as a raw material; and a method of forming the thin film. A compound represented by the general formula (1) is produced by reacting a compound represented by the general formula (2) with a compound represented by the general formula (3). The compound produced is used as a raw material to form a metal-containing thin film. [Chemical formula 1] (1) [Chemical formula 2] (2) [Chemical formula 3] $M_p(NR^4R^5)_q$ (3) (In the formulae, M represents a Group 4 element, aluminum, gallium, etc.; n is 2 or 3 according to cases; $R^1$ and $R^3$ each represents $C_{1-6}$ alkyl, etc.; $R^2$ represents $C_{1-6}$ alkyl, etc.; $R^4$ and $R^5$ each represents $C_{1-4}$ alkyl, etc.; X represents hydrogen, lithium, or sodium; p is 1 or 2 according to cases; and q is 4 or 6 according to cases).

[Chem. 1]

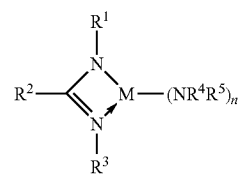

(1)

[Chem. 2]

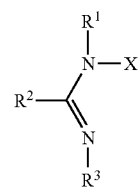

(2)

11 Claims, 7 Drawing Sheets

US 7,816,549 B2

METAL-CONTAINING COMPOUND, ITS PRODUCTION METHOD, METAL-CONTAINING THIN FILM, AND ITS FORMATION METHOD

TECHNICAL FIELD

The present invention relates to a raw material compound of a metal-containing thin film useful for, for example, production of a semiconductor element, its production method, a metal-containing thin film, and its formation method.

BACKGROUND ART

Until now, titanium, titanium nitride, silicon-containing titanium nitride and the like have been used as a raw material for a wiring barrier film in a semiconductor device. Furthermore, silicon oxynitride (SiON) and alumina ($Al_2O_3$) are used as main raw materials in a DRAM capacitor dielectric of a semiconductor device which has heretofore been developed. Moreover, silica ($SiO_2$) has been used as a main raw material in a gate insulating film of a semiconductor device. However, miniaturization of a device is required in the next generation semiconductor in order to meet high performance, and a material having further high dielectric constant is required in a raw material of a capacitor dielectric and a gate insulating film. At the present time, titanium oxide, zirconium oxide, hafnium oxide and a composite oxide containing those metals, aluminum and the like are noted as a novel material used in those sites.

A formation method of a thin film now used as a semiconductor element includes a physical vapor deposition method (PVD method) by sputtering, and a chemical vapor deposition method (CVD method). However, in a semiconductor production in the next generation or later, it is required to form a uniform and thin film on a surface having a complicated three-dimensional structure of a miniaturized element. PVD method is not suitable as a method of forming a uniform thin film on a surface having concave and convex, i.e., a method of preparing a thin film having good step coverage. For this reason, a thin film formation method by CVD method which sends a raw material in a form of a gas to a reaction chamber and decomposes the same to deposit a thin film, or an atomic layer deposition method (ALD method) which adsorbs a raw material on a substrate surface and decomposes the same to deposit a thin film is investigated.

In a semiconductor element production, a raw material that has appropriate vapor pressure and thermal stability and can vaporize in a stable supply amount is selected as a raw material for forming a thin film by CVD method or ALD method. Furthermore, it is one of necessary conditions that a material can be film-formed with uniform thickness on a surface having a complicated three-dimensional structure. Moreover, it is preferred that a raw material is liquid when supplied.

Titanium tetrachloride $TiCl_4$, tetrakisamide complex $Ti(NRR')_4$ (R and R' are a methyl group or an ethyl group) and the like are investigated as a raw material that forms a titanium thin film, a titanium nitride film and a silicon-containing titanium nitride film, used in a wiring barrier and an electrode film of a capacitor by CVD method or ALD method.

Chlorine remains in a thin film formed by $TiCl_4$ of the above raw materials, and high temperature is required to completely remove chlorine. For this reason, $TiCl_4$ is not suitable as a raw material for forming a thin film on a portion which requires film formation at low temperature and a portion to which residual chlorine adversely affects.

It is known that $Ti(NRR')_4$ has extremely high reactivity to water and reacts with a slight amount of water contained in a carrier gas, a reaction gas or the like used in film formation, and oxygen is liable to be incorporated in a film formed. For example, it is reported that 10 atm % or more of oxygen is contained in a titanium nitride thin film formed by a remote plasma ALD method using tetrakis(dimethylamido)titanium $Ti(NMe_2)_4$ as a raw material (Non-Patent Document 1). A thin film containing oxygen has high specific resistance value, and therefore, does not satisfy the demand characteristics of a barrier layer. In other words, those tetrakisamide complexes are not suitable as a raw material for barrier layer formation.

On the other hand, tetraisopropoxotitanium $Ti(O^iPr)_4$, (bisisopropoxo)(bis(2,2,6,6-tetramethylheptanedionato))-titanium $Ti(O^iPr)_2(THD)_2$ tetrakis(2-methoxy-1-methyl-1-propoxo)titanium $Ti(MMP)_4$ and the like are investigated as raw materials for forming a titanium oxide thin film and a titanium-containing oxide thin film used in a capacitor dielectric film by CVD method of ALD method.

Where it is attempted to form a thin film using $Ti(O^iPr)_4$ as a raw material, $Ti(O^iPr)_4$ has extremely high reactivity to water, and as a result, there is the possibility that contamination of a slight amount of water vapor into a piping in an apparatus forms fine powder of titanium oxide, thereby clogging a pipe. Furthermore, where $Ti(O^iPr)_4$ is blown to a substrate and decomposed thereon, an alcohol is generated, and the alcohol is decomposed into water and an alkene. Water reacts with undecomposed $Ti(O^iPr)_4$ to form a fine powder of titanium oxide, and the fine powder is adhered to a film formation chamber and a discharge port, resulting in the decrease of productivity. For this reason, $Ti(O^iPr)_4$ is not suitable as a raw material for the formation of a thin film used in a semiconductor element (see Patent Document 1).

Where a thin film is formed using $Ti(O^iPr)_2(THD)_2$ or $Ti(MMP)_4$, particularly where a titanium-containing composite oxide thin film is formed by CVD method, volatilization properties and decomposition properties of those to other metal supply source raw materials greatly differ, and as a result, there was the problem that it is difficult to control a composition of a thin film, thereby decreasing productivity.

There are examples that $ZrCl_4$, $Zr(acac)_4$ (acac=acetylacetonate), $Zr(tmhd)_4$, (tmhd=2,2,6,6-tetramethyl-3,5-heptanedionate) and the like are used as raw materials of a zirconium oxide thin film or a zirconium-containing composite oxide thin film by CVD method or ALD method. However, those materials each have low vapor pressure, and are not preferred as a raw material for the synthesis of a thin film by CVD method or ALD method. $Zr(O^tBu)_4$ ($^tBu$=tert-butyl) has good vapor pressure, but has the disadvantage that a film formation temperature is high. Tetrakisamide complexes $Zr(NRR')_4$ (R and R' are a methyl group or an ethyl group) are also investigated. However, those tetrakisamide complexes are slightly poor in thermal stability, and are not preferred as a raw material for the synthesis of a thin film by CVD method or ALD method (Non-Patent Document 2).

$HfCl_4$, $Hf(acac)_4$ (acac=acetylacetonate), $Hf(tmhd)_4$ (tmhd=2,2,6,6-tetramethyl-3,5-heptanedionate), $Hf(O^tBu)_4$ ($^tBu$=tert-butyl), and additionally tetrakisamide complexes $Hf(NRR')_4$ (R and R' are a methyl group or an ethyl group) are investigated as raw materials of a hafnium oxide thin film or a hafnium-containing composite oxide thin film by CVD method or ALD method. Problems of those raw materials are described in Non-Patent Document 3.

Of the above raw materials, $HfCl_4$ has low volatility and requires high temperature to form an oxide film. Therefore, $HfCl_4$ is not suitable as a raw material for the formation of a thin film used in a semiconductor element. HfCl(tmhd)$_3$ and HfCl$_2$(tmhd)$_2$ containing a chlorine atom are investigated (see Patent Document 2), but their vaporization temperature is high and those are not satisfactory raw materials.

An example that a hafnium oxide thin film was formed by ALD method using tetrakisamide complexes Hf(NRR')$_4$ as a raw material is reported (Non-Patent Document 2). However, it is described in Non-Patent Document 2 that thermal stability of tetrakisamide complexes is low, and it is reported that, for example, tetrakis(dimethylamido)hafnium Hf (NMe$_2$)$_4$ gradually decomposes at 90° C., and tetrakis(ethylmethylamido)hafnium Hf(NMeEt)$_4$ gradually decomposes at 140° C. As a result that the present inventors actually investigated thermal stability of Hf(NMeEt)$_4$ by heating the same at 150° C. for 120 hours, it was confirmed that 78% of Hf(NMeEt)$_4$ decomposes. In other words, it is difficult to say that those tetrakisamide complexes have sufficient thermal stability as an industrial raw material for thin film formation.

An alkyl aluminum compound such as trimethyl aluminum, and an amide aluminum compound such as hexakis-(diethylamido)dialuminum have been investigated as an aluminum compound for forming a composite oxide thin film of aluminum and titanium, zirconium or hafnium. However, the alkyl aluminum is a spontaneously combustible substance or a water-prohibiting substance, and instantaneously combusts by the contact with a slight amount of air, thus being dangerous. To use those substances, there is the problem that specific facilities must be provided. Furthermore, an amide aluminum compound has a dinuclear structure, and as a result, vapor pressure thereof is low. Therefore, the amide aluminum compound is not suitable as a raw material for thin film formation by CVD method or ALD method.

A trialkyl gallium is investigated as a raw material in forming a gallium nitride thin film or a gallium arsenic thin film for use as a semiconductor. However, those are a spontaneously combustible substance or a water-prohibiting substance, similar to a trialkyl aluminum, and to use those, there is the problem that special facilities must be provided.

Non-Patent Document 1: Journal of The Electrochemical Society, 152, G29 (2005)

Non-Patent Document 2: Chemistry of Materials, 14, 4350 (2002)

Non-Patent Document 3: Journal of Materials Chemistry, 14, 3101 (2004)

Patent Document 1: JP-A-2004-196618

Patent Document 2: JP-A-2003-137551

DISCLOSURE OF THE INVENTION

Problems that the Invention is to Solve

Objects of the present invention are to provide a novel compound that has an appropriate thermal stability, an appropriate volatility and an appropriate stability to water and air, and becomes a raw material for forming a metal-containing thin film by methods such as CVD method or ALD method, its production method, a thin film using the same, and its formation method.

Means for Solving the Problems

As a result of extensive and intensive investigations in view of the above-described present situation, the present inventors have found that a compound having an amidinate ligand represented by the general formula (1) is an excellent compound that can solve the above-described problems, and have reached to complete the present invention.

That is, the present invention relates to a compound represented by the general formula (1)

[Chem. 1]

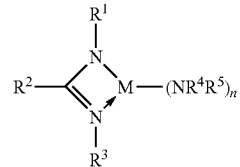

(1)

(In the formula, M represents a Group 4 atom, an aluminum atom, a gallium atom or an indium atom. When M is a Group 4 atom, n is 3, and when M is an aluminum atom, a gallium atom or an indium atom, n is 2. $R^1$ and $R^3$ each independently represent an alkyl group having from 1 to 6 carbon atoms which may be substituted with a fluorine atom, or a trialkylsilyl group represented by $R^6R^7R^8Si$. $R^6$, $R^7$ and $R^8$ each independently represent an alkyl group having from 1 to 4 carbon atoms. $R^2$ represents a hydrogen atom or an alkyl group having from 1 to 6 carbon atoms which may be substituted with a fluorine atom. $R^2$ and $R^3$ may be combined to form a ring. $R^4$ and $R^5$ each independently represent an alkyl group having from 1 to 4 carbon atoms which may be substituted with a fluorine atom.).

The present invention further relates to a production method of the compound represented by the general formula (1), which comprises reacting a compound represented by the general formula (3)

$$M_p(NR^4R^5)_q \quad (3)$$

(In the formula, M, $R^4$ and $R^5$ are the same as defined above. When M is a Group 4 atom, p is 1 and q is 4. When M is an aluminum atom, a gallium atom or an indium atom, p is 2 and q is 6)

with a compound represented by the general formula (2)

[Chem. 2]

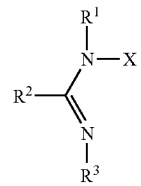

(2)

(In the formula, $R^1$, $R^2$ and $R^3$ are the same as defined above. X represents a hydrogen atom, a lithium atom or a sodium atom.).

The present invention further relates to an M-containing thin film (M is the same as defined above) formed by using the compound represented by the general formula (1) as a raw material.

The present invention further relates to a formation method of an M-containing thin film (M is the same as defined above), which comprises using the compound represented by the general formula (1) as a raw material.

Advantage of the Invention

The compound of the present invention has an appropriate thermal stability, an appropriate volatility and an appropriate stability to water and air, and can form a metal-containing thin film by CVD method or ALD method using those.

DESCRIPTION OF REFERENCE NUMERALS AND SIGNS

Figure 1:
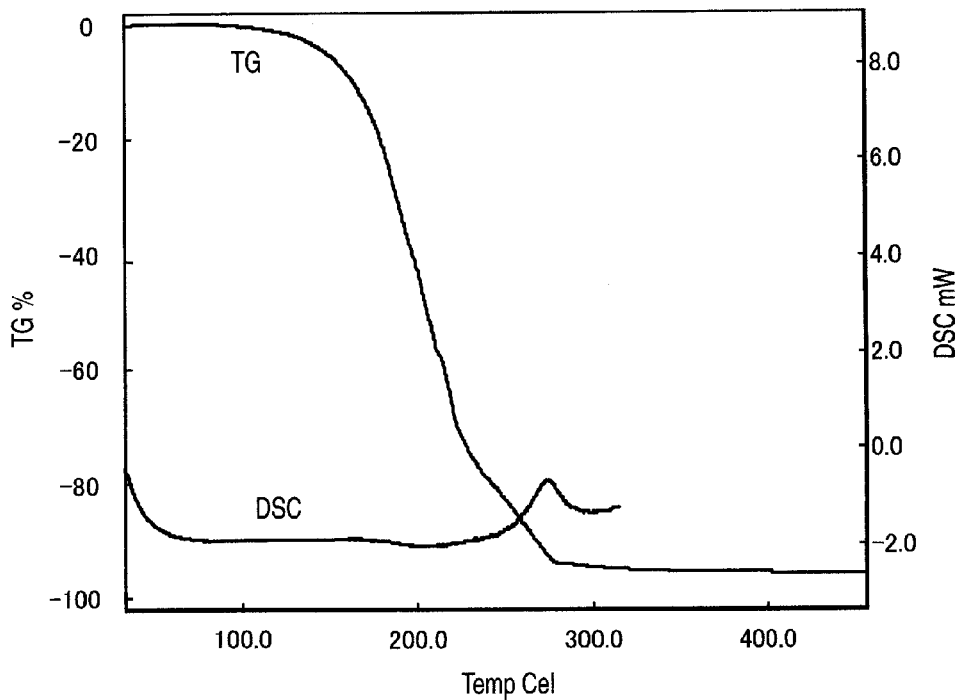
FIG. 1 is the result of TG and DSC measurements of Ti($^i$PrNC(Me)N$^i$Pr)(NMe$_2$)$_3$.

1. Raw material vessel
2. Thermostatic bath
3. Reaction chamber
4. Substrate
5. Reaction gas
6. Diluent gas
7. Carrier gas
8. Mass flow controller
9. Mass flow controller
10. Mass flow controller
11. Vacuum pump
12. Exhaust

BEST MODE FOR CARRYING OUT THE INVENTION

The present invention is described in more detail below.
The compound of the present invention represented by the general formula (1) is capable of having a resonance structure represented by the following general formula (4)

[Chem. 4]

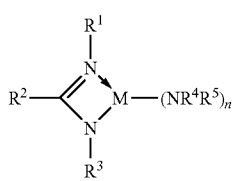

(4)

(In the formula, M, n, $R^1$, $R^2$, $R^3$, $R^4$ and $R^5$ are the same as defined above), and is actually a resonance hybrid of a compound represented by the general formula (1) and a compound represented by the general formula (4). In the present description, those compounds are combined and the combination is represented by the general formula (1) for simplicity.

Examples of the alkyl group having from 1 to 6 carbon atoms represented by $R^1$, $R^2$ and $R^3$ include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclopropyl group, a cyclobutyl group, a cyclopentyl group, a cyclohexyl group, a cyclopropylmethyl group, a cyclopropylethyl group and a cyclobutylmethyl group.

Those alkyl groups may be substituted with a fluorine atom, and examples thereof include a trifluoromethyl group, a 2,2,2-trifluoroethyl group, a perfluoroethyl group, a perfluoropropyl group, a perfluoroisopropyl group, a perfluorobutyl group, a perfluoro-sec-butyl group, a perfluoro-tert-butyl group, a perfluoropentyl group and a perfluorohexyl group.

Examples of the trialkylsilyl group represented by $R^6R^7R^8Si$ include a trimethylsilyl group, a triethylsilyl group, an ethyldimethylsilyl group, a diethylmethylsilyl group, a dimethylpropylsilyl group and a tert-butyl-dimethylsilyl group.

Examples of the ring which may be formed by combining $R^2$ and $R^3$ include a pyrrole ring, a pyrrolidine ring and a piperidine ring.

Examples of the alkyl group having from 1 to 4 carbon atoms represented by $R^4$ and $R^5$ include a methyl group, an ethyl group, a propyl group, an isopropyl group, a butyl group, an isobutyl group, a sec-butyl group and a tert-butyl group. Those alkyl groups may be substituted with a fluorine atom, and examples thereof include a trifluoro-methyl group, a 2,2,2-trifluoroethyl group, a perfluoro-ethyl group, a perfluoropropyl group, a perfluoroisopropyl group, a perfluorobutyl group, a perfluoro-sec-butyl group and a perfluoro-tert-butyl group.

M represents a Group 4 atom, an aluminum atom, a gallium atom or an indium atom. Above all, a Group 4 atom, an aluminum atom and a gallium atom are preferred. The Group 4 atom means a titanium atom, a zirconium atom and a hafnium atom.

From the point that the compound represented by the general formula (1) has good vapor pressure, $R^1$ and $R^3$ are preferably an isopropyl group or a tert-butyl group, $R^2$ is preferably a hydrogen atom, a methyl group or an ethyl group, and $R^4$ and $R^5$ are preferably a methyl group or an ethyl group. In particular, when M is a Group 4 atom, a compound wherein $R^1$ and $R^3$ are an isopropyl group, $R^2$ is a methyl group, and $R^4$ and $R^5$ are a methyl group, or a compound wherein $R^1$ and $R^3$ are a tert-butyl group, $R^2$ is a hydrogen atom, and $R^4$ and $R^5$ are a methyl group, is particularly preferred. Furthermore, when M is an aluminum atom, a gallium atom or an indium atom, a compound wherein $R^1$ and $R^3$ are an isopropyl group, $R^2$ is a methyl group, and $R^4$ and $R^5$ are a methyl group is particularly preferred.

X in the general formula (2) is preferably a hydrogen atom or a lithium atom, and more preferably a hydrogen atom, from the point that the yield of the compound represented by the general formula (1) is good.

The compound represented by the general formula (1) can be produced by reacting the compound represented by the general formula (2) and the compound represented by the general formula (3) in an argon or nitrogen atmosphere. This reaction proceeds without using a solvent, but the reaction is preferably conducted in an organic solvent. Examples of the organic solvent used in the reaction include hydrocarbons such as pentane, hexane, heptane, octane, benzene, toluene, ethylbenzene and xylene; ethers such as diethyl ether, diisopropyl ether, glyme, dioxane, tetrahydrofuran and cyclopentylmethyl ether; and amines such as triethylamine and diethylisopropylamine. Those organic solvents can be used alone or as mixtures thereof. Tetrahydrofuran, hexane or heptane is preferably used from the point of good yield.

The reaction temperature is not particularly limited, but when the reaction temperature is appropriately selected from a range of from −20 to 120° C., the desired product can be obtained in good yield. The reaction time is not limited, but when the reaction time is appropriately selected from a range of from 1 minute to 24 hours, the reaction can be completed. After completion of the reaction, the reaction mixture is concentrated, and if necessary, filtered, to obtain a crude product. The crude product can be distilled or sublimated to purify the desired product.

The compound represented by the general formula (2) as a raw material can be synthesized by reference to the conventional methods (for example, Nagashima et al., Orgnometallics, 19, 725, (2000); Forsberg et al., The Journal of Organic Chemistry, 52, 1017, (1987); and US-A-2005/0042372). The compound represented by the general formula (3) can be synthesized by reference to the conventional methods (for example, Bradley et al., Journal of the Chemical Society, 3857, (1960), and Power et al., Polyhedron, 9, 257, (1990)).

A metal-containing thin film can be formed using the compound represented by the general formula (1) as a raw material. For example, when the metal-containing thin film is formed by CVD method or ALD method, the compound represented by the general formula (1) is gasified and supplied onto a substrate. The gasification method includes, for example, a method of introducing a raw material into a heated thermostatic bath, and blowing a carrier gas such as helium, neon, argon, krypton, xenon or nitrogen therein, and gasifying, and a method of feeding the compound represented by the general formula (1) directly or in a form of a solution to a carburetor, and heating the same to gasify in the carburetor. The solvent used in the case of the latter method is not particularly limited, and examples thereof include ethers such as glyme, diglyme, triglyme, dioxane, tetrahydrofuran and cyclopentylmethyl ether; and hydrocarbons such as hexane, cyclohexane, methyl cyclohexane, ethyl cyclohexane, heptane, octane, nonane, decane, benzene, toluene, ethylbenzene and xylene.

A metal-containing thin film can be formed by decomposing a raw material as a gas supplied onto a substrate. The decomposition can be performed by only heating, but plasma or light may be used in combination. Furthermore, the decomposition may be conducted by the co-presence of a reactive gas such as water vapor, oxygen, ozone, hydrogen or ammonia.

The present invention is described in more detail by reference to the Examples, but the invention is not construed as being limited to those Examples. In the symbols used in the present description, Me means a methyl group, Et means an ethyl group, $^i$Pr means an isopropyl group, and $^t$Bu means a tert-butyl group.

Reference Example 1

Synthesis of N,N'-diisopropyl acetamidine 30.0 g of trimethyl orthoacetate, 15.0 g of acetic acid and 30.0 g of isopropylamine were placed in a flask, and refluxed under heating for 12 hours. The flask was cooled to room temperature, and 200 ml of heptane and 48.3 g of a methanol solution of sodium methoxide (28%) were added thereto. After stirring at room temperature for 1 hour, fractions having a distillation temperature of 95° C. or lower were removed under atmospheric pressure. After cooling the flask to room temperature, 45 ml of water was added thereto, and the resulting mixture was vigorously stirred for 10 minutes. The mixture was allowed to stand for 30 minutes to separate the same into two layers, and an aqueous layer was removed. An oil remained after concentrating an organic layer was distilled under reduced pressure to obtain 28.5 g of N,N'-diisopropylacetamidine (yield 80%).

$^1$H NMR (500 MHz, CDCl$_3$, δ/ppm) 3.62 (br, 2H), 1.84 (br, s, 3H), 1.09 (d, J=7 Hz, 12H)

Reference Example 2

Synthesis of N,N'-di-tert-butylformamidine 148.2 g of triethyl orthoformate and 60.0 g of acetic acid were placed in a flask, and 146.5 g of tert-butylamine was introduced therein while stirring. After refluxing under heating from 12 hours, the flask was cooled to room temperature, and 500 ml of heptane and 193.0 g of a methanol solution of sodium methoxide (28%) were added thereto. After stirring at room temperature for 1 hour, fractions having a distillation temperature of 95° C. or lower were removed under atmospheric pressure. After cooling the flask to room temperature, 150 ml of water was added thereto, and the resulting mixture was vigorously stirred for 10 minutes. The mixture was allowed to stand for 30 minutes to separate the same into two layers, and an aqueous layer was removed. An oil remained after concentrating an organic layer was distilled under reduced pressure to obtain 103.6 g of N,N'-di-tert-butylformamidine (yield 66%).

$^1$H NMR (500 MHz, CDCl$_3$, δ/ppm) 7.48 (s, 1H), 1.17 (s, 18H)

Reference Example 3

Synthesis of N,N'-diisopropylpropioamidine 44.9 g of triethyl orthopropionate and 15.3 g of acetic acid were placed in a flask, and 30.3 g of isopropylamine was introduced therein while stirring. After refluxing under heating for 12 hours, the flask was cooled to room temperature, and 100 ml of heptane and 48.4 g of a methanol solution of sodium methoxide (28%) were added thereto. After stirring at room temperature for 1 hour, fractions having a distillation temperature of 95° C. or lower were removed under atmospheric pressure. After cooling the flask to room temperature, 45 ml of water was added thereto, and the resulting mixture was vigorously stirred for 10 minutes. The mixture was allowed to stand for 30 minutes to separate the same into two layers, and an aqueous layer was removed. An oil remained after concentrating an organic layer was distilled under reduced pressure to obtain 26.3 g of N,N'-diisopropylpropioamidine (yield 66%).

$^1$H NMR (500 MHz, CDCl$_3$, δ/ppm) 3.63 (br, 2H), 2.08 (br, q, J=7 Hz, 2H), 1.04 (t, J=7 Hz, 3H), 1.03 (d, J=7 Hz, 12H)

Example 1

Synthesis of (N,N'-diisopropylacetamidinato)tris(dimethylamido)titanium (Ti($^i$PrNC(Me)N$^i$Pr)(NMe$_2$)$_3$)

In an argon atmosphere, a solution of 2.24 g (10.0 mmol) of tetrakis(dimethylamido)titanium dissolved in 30 ml of hexane was cooled to 4° C., and 1.43 g (10.0 mmol) of N,N'-diisopropylacetamidine was added dropwise thereto. After stirring the resulting mixture at room temperature for 12 hours, a solvent was distilled away under reduced pressure. A residue obtained was distilled under reduced pressure to obtain 1.58 g of a red liquid (yield 49%).

$^1$H NMR (500 MHz, C$_6$D$_6$, δ/ppm) 3.37 (sept., J=7 Hz, 2H), 3.29 (s, 18H), 1.55 (s, 3H), 1.04 (d, J=7 Hz, 12H)

$^{13}$C NMR (125 MHz, C$_6$D$_6$, δ/ppm) 174.0, 48.7, 46.5, 25.1, 10.4

Thermal analysis of Ti($^i$PrNC(Me)N$^i$Fr)(NMe$_2$)$_3$

The result of TG (thermogravimetric determination) measured at a temperature rising rate of 10° C./min under argon flow (400 ml/min) and the result of DSC (differential scanning calorimetry) measured at a temperature rising rate of 10° C./min in a closed vessel were shown in FIG. 1. It was seen from TG to have vaporization properties suitable as a raw material of CVD method or ALD method, and it was seen from DSC that thermal stability is good.

Example 2

Synthesis of (N,N'-diisopropylpropioamidinato)tris(dimethylamido)titanium (Ti($^i$PrNC(Et)N$^i$Pr)(NMe$_2$)$_3$)

In an argon atmosphere, a solution of 3.43 g (15.3 mmol) of tetrakis(dimethylamido)titanium dissolved in 15 ml of tetrahydrofuran was cooled to −20° C., and 2.39 g (15.3 mmol) of N,N'-diisopropylpropioamidine was added dropwise thereto. After stirring at room temperature for 12 hours, a solvent was distilled away under reduced pressure. A residue obtained was distilled under reduced pressure to obtain 4.68 g of a red liquid (yield 91%).

$^1$H NMR (500 MHz, C$_6$D$_6$, δ/ppm) 3.43 (sept., J=6 Hz, 2H), 3.30 (s, 18H), 2.03 (q, J=8 MHz, 2H), 1.08 (d, J=7 Hz, 12H), 0.94 (t, J=8 Hz, 3H)

$^{13}$C NMR (125 MHz, C$_6$D$_6$, δ/ppm) 178.6, 48.5, 46.8, 25.6, 18.1, 12.3

Thermal analysis of Ti($^i$PrNC(Et)N$^i$Fr)(NMe$_2$)$_3$

Figure 2:
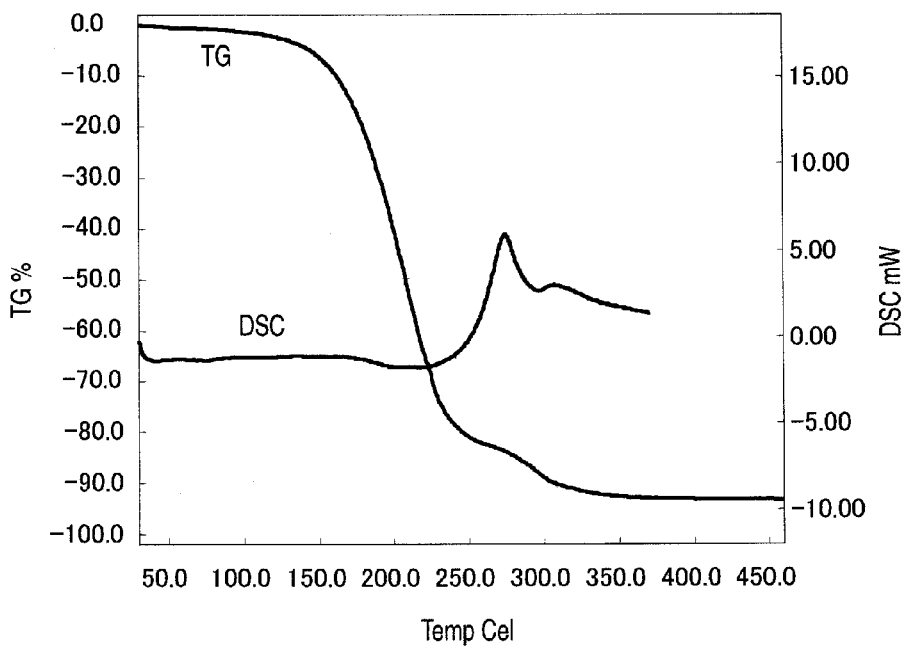
FIG. 2 is the result of TG and DSC measurements of Ti($^i$PrNC(Et)N$^i$Pr)(NMe$_2$)$_3$.

The result of TG (thermogravimetric determination) measured at a temperature rising rate of 10° C./min under argon flow (400 ml/min) and the result of DSC (differential scanning calorimetry) measured at a temperature rising rate of 10° C./min in a closed vessel were shown in FIG. 2. It was seen from TG to have vaporization properties suitable as a raw material of CVD method or ALD method, and it was seen from DSC that thermal stability is good.

Example 3

Synthesis of (N,N'di-tert-butylformamidinato)tris(dimethyl-amido)titanium (Ti($^t$BuNC(H)N$^t$Bu)(NMe$_2$)$_3$)

In an argon atmosphere, a solution of 14.2 g (63.4 mmol) of tetrakis(dimethylamido)titanium dissolved in 40 ml of tetrahydrofuran was cooled to 4° C., and 10.0 g (64.0 mmol) of N,N'di-tert-butylformamidine was added dropwise thereto. After stirring at room temperature for 12 hours, a solvent was distilled away under reduced pressure. A residue obtained was distilled under reduced pressure to obtain 15.7 g of a red liquid (yield 74%).

$^1$H NMR (500 MHz, C$_6$D$_6$, δ/ppm) 8.58 (s, 1H), 3.29 (s, 18H), 1.14 (s, 18H)

$^{13}$C NMR (125 MHz, C$_6$D$_6$, δ/ppm) 163.4, 54.1, 46.7, 31.7

Thermal analysis of Ti($^t$BuNC(H)N$^t$Bu)(NMe$_2$)$_3$

Figure 3:
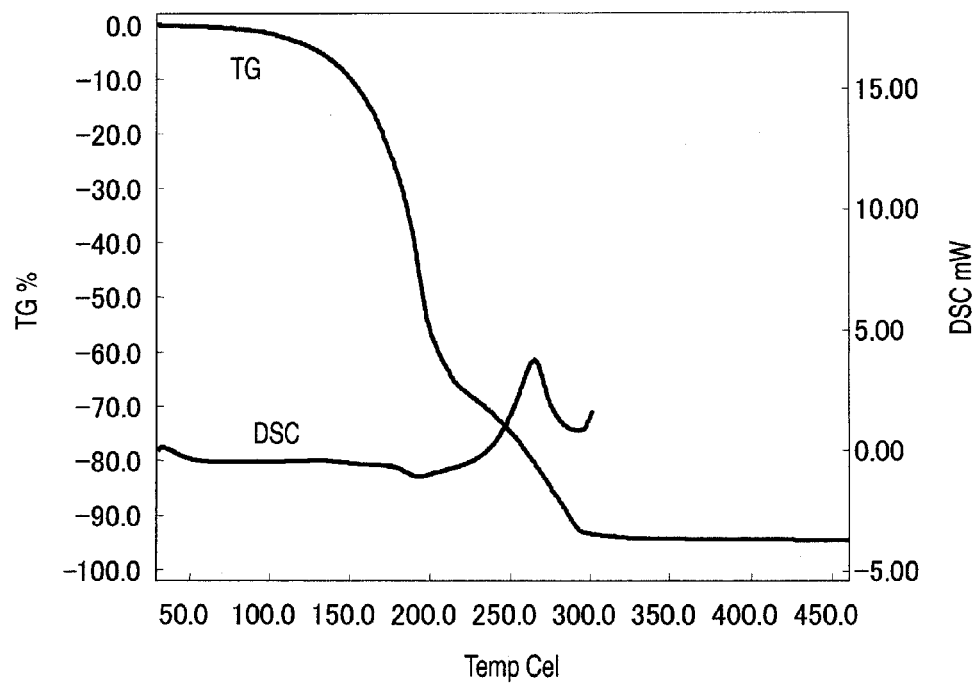
FIG. 3 is the result of TG and DSC measurements of Ti($^t$BuNC(H)N$^t$Bu)(NMe$_2$)$_3$.

The result of TG (thermogravimetric determination) measured at a temperature rising rate of 10° C./min under argon flow (400 ml/min) and the result of DSC (differential scanning calorimetry) measured at a temperature rising rate of 10° C./min in a closed vessel were shown in FIG. 3. It was seen from TG to have vaporization properties suitable as a raw material of CVD method or ALD method, and it was seen from DSC that thermal stability is good.

Example 4

Synthesis of (N,N'-diisopropylacetamidinato)tris(dimethylamido)zirconium (Zr($^i$PrNC(Me)N$^i$Pr)(NMe$_2$)$_3$)

In an argon atmosphere, 3.08 g (21.7 mmol) of N,N'-diisopropylacetamidine was added to a solution of 5.20 g (19.4 mmol) of tetrakis(dimethylamido)zirconium dissolved in 20 ml of hexane. After stirring at room temperature for hours, a solvent was distilled away under reduced pressure. A residue obtained was distilled under reduced pressure to obtain 2.30 g of a colorless liquid (yield 32%).

$^1$H NMR (500 MHz, C$_6$D$_6$, δ/ppm) 3.33 (sept., J=6 Hz, 2H), 3.12 (s, 18H), 1.49 (s, 3H), 1.05 (d, J=6 Hz, 12H)

$^{13}$C NMR (125 MHz, C$_6$D$_6$, δ/ppm) 175.7, 48.1, 43.0, 25.3, 10.7

Thermal analysis of Zr($^i$PrNC(Me)N$^i$Pr)(NMe$_2$)$_3$

Figure 4:
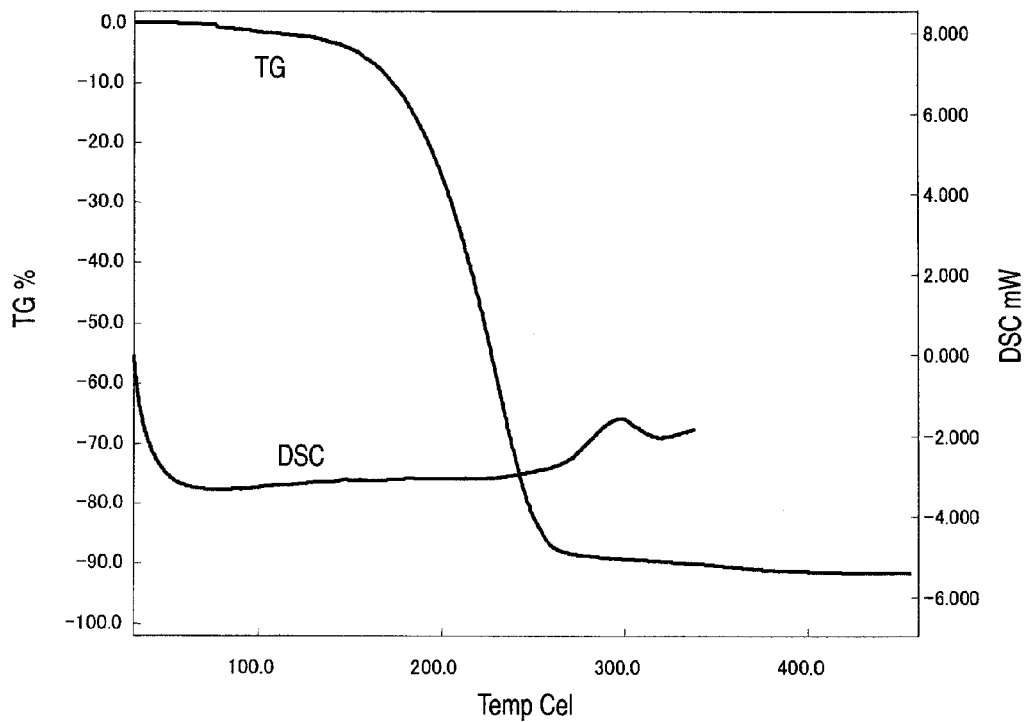
FIG. 4 is the result of TG and DSC measurements of Zr($^i$PrNC(Me)N$^i$Pr)(NMe$_2$)$_3$.

The result of TG (thermogravimetric determination) measured at a temperature rising rate of 10° C./min in an atmosphere which flows argon at 400 ml/min and the result of DSC (differential scanning calorimetry) measured at a temperature rising rate of 10° C./min in a closed vessel were shown in FIG. 4. It was seen from TG to have vaporization properties suitable as a raw material of CVD method or ALD method, and it was seen from DSC that thermal stability is good.

Example 5

Synthesis of (N,N'-diisopropylpropioamidinato)tris(dimethylamido)zirconium (Zr($^i$PrNC(Et)N$^i$Pr)(NMe$_2$)$_3$)

In an argon atmosphere, a solution of 1.78 g (6.66 mmol) of tetrakis(dimethylamido)zirconium dissolved in a mixture of 8 ml of tetrahydrofuran and 1 ml of triethylamine was cooled to −20° C., and 1.04 g (6.66 mmol) of N,N'-diisopropylpropioamidine was added dropwise thereto. After stirring at room temperature for 4 hours, a solvent was distilled away under reduced pressure. A residue obtained was distilled under reduced pressure to obtain 1.51 g of a pale yellow liquid (yield 60%).

$^1$H NMR (500 MHz, C$_6$D$_6$, δ/ppm) 3.39 (sept., J=6 Hz, 2H), 3.12 (s, 18H), 2.00 (q, J=8 Hz, 2H), 1.08 (d, J=7 Hz, 12H), 0.90 (t, J=8 Hz, 3H)

$^{13}$C NMR (125 MHz, C$_6$D$_6$, δ/ppm) 179.8, 47.7, 43.0, 25.7, 18.2, 12.5

Thermal analysis of Zr($^i$PrNC(Et)N$^i$Fr)(NMe$_2$)$_3$

Figure 5:
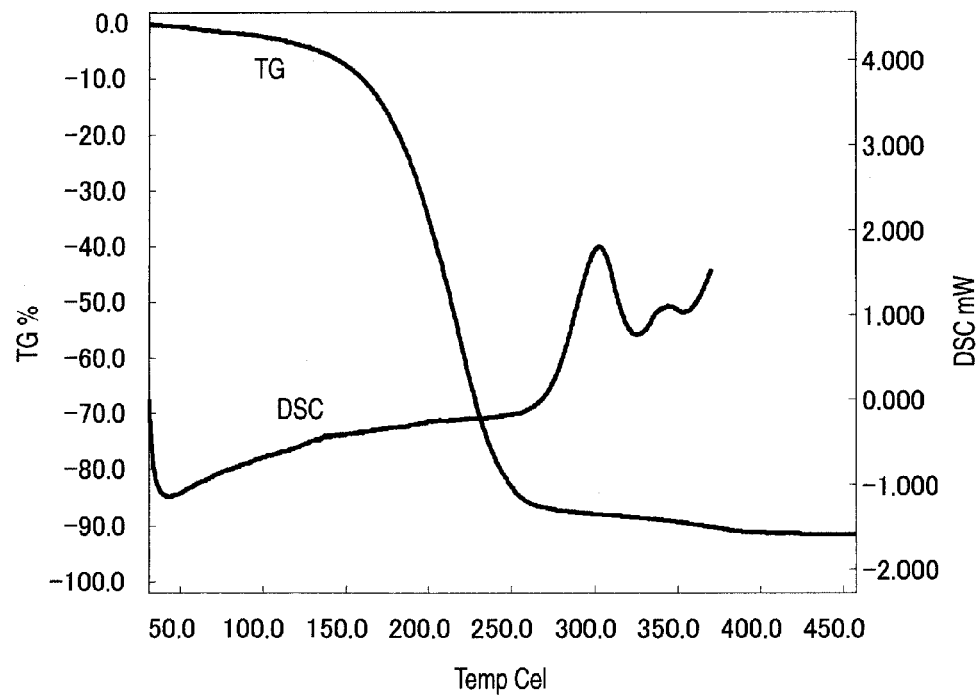
FIG. 5 is the result of TG and DSC measurements of Zr($^i$PrNC(Et)N$^i$Pr)(NMe$_2$)$_3$.

The result of TG (thermogravimetric determination) measured at a temperature rising rate of 10° C./min under argon flow (400 ml/min) and the result of DSC (differential scanning calorimetry) measured at a temperature rising rate of 10° C./min in a closed vessel were shown in FIG. 5. It was seen from TG to have vaporization properties suitable as a raw material of CVD method or ALD method, and it was seen from DSC that thermal stability is good.

Example 6

Synthesis of (N,N'-di-tert-butylformamidinato)tris(dimethyl-amido)zirconium (Zr($^t$BuNC(H)N$^t$Bu)(NMe$_2$)$_3$)

In an argon atmosphere, 7.4 ml of a hexane solution (1.59M) of butyl lithium was diluted with 15 ml of hexane, and resulting mixture was cooled to –20° C. After adding 1.79 g of N,N'-di-tert-butylformamidine, the resulting mixture was stirred at room temperature for 12 hours. The resulting reaction solution was cooled to –20° C., and a solution of 3.04 g (11.4 mmol) of tetrakis(dimethylamido)zirconium dissolved in 10 ml of hexane was added thereto. After stirring at room temperature for 4 hours, 1.57 g of triethylamine hydrochloride was added, followed by stirring at room temperature for 2 hours. The resulting reaction solution was filtered to remove insoluble matters, and a solvent was distilled away from a filtrate under reduced pressure. A residue obtained was distilled under reduced pressure to obtain 1.98 g of a colorless liquid (yield 46%).

$^1$H NMR (500 MHz, C$_6$D$_6$, δ/ppm) 8.56 (s, 1H), 3.11 (s, 18H), 1.12 (s, 18H)

$^{13}$C NMR (125 MHz, C$_6$D$_6$, δ/ppm) 164.8, 53.4, 42.9, 31.6

Thermal analysis of Zr($^t$BuNC(H)N$^t$Bu)(NMe$_2$)$_3$

Figure 6:
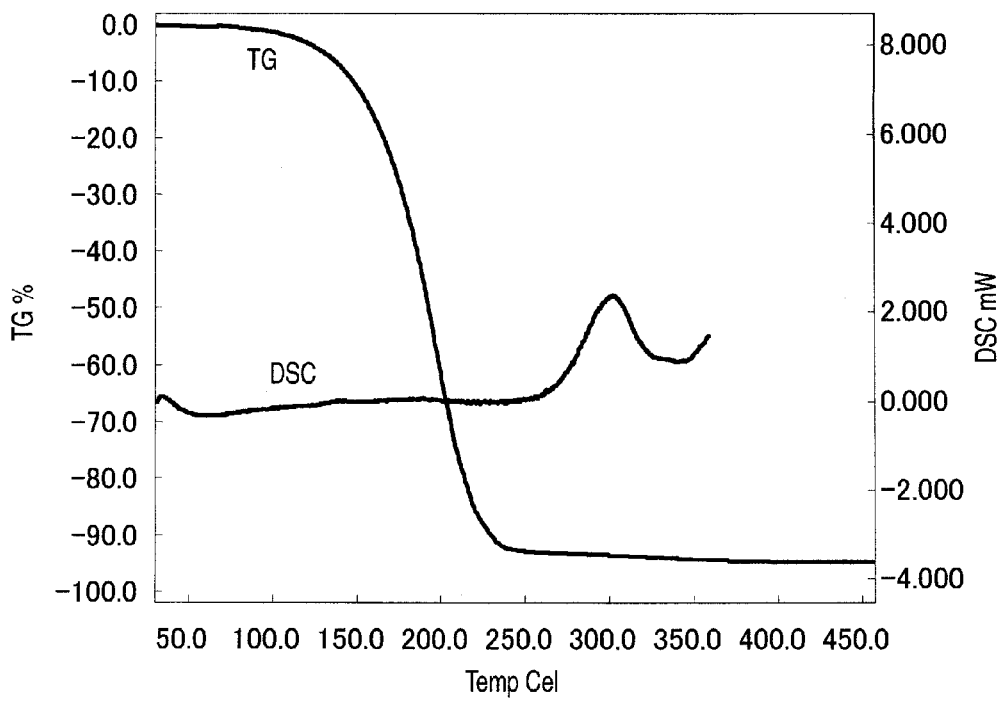
FIG. 6 is the result of TG and DSC measurements of Zr($^t$BuNC(H)N$^t$Bu)(NMe$_2$)$_3$.

The result of TG (thermogravimetric determination) measured at a temperature rising rate of 10° C./min in an atmosphere which flows argon at 400 ml/min and the result of DSC (differential scanning calorimetry) measured at a temperature rising rate of 10° C./min in a closed vessel were shown in FIG. 6. It was seen from TG to have vaporization properties suitable as a raw material of CVD method or ALD method, and it was seen from DSC that thermal stability is good.

Example 7

Synthesis of (N,N'-di-tert-butylacetamidinato)tris(dimethyl-amido)zirconium (Zr($^t$BuNC(Me)N$^t$Bu)(NMe$_2$)$_3$)

In an argon atmosphere, 970 mg (6.29 mmol) of N,N'-di-tert-butylcarbodiimide was dissolved in 5 ml of hexane, and 5.70 ml (6.10 mmol) of a diethyl ether solution (1.07 mol/l) of methyl lithium was added thereto, followed by stirring at room temperature for 12 hours. A solvent was distilled away under reduced pressure. A white solid obtained was suspended in 5 ml of hexane, and a solution of 1.62 g (6.06 mmol) of tetrakis(dimethylamido)zirconium dissolved in 5 ml of hexane was added thereto, followed by stirring at 50° C. for 4 hours. After cooling to room temperature, insoluble matters were filtered off using a glass filter, and hexane was distilled away from a filtrate under reduced pressure. A residue obtained was distilled under reduced pressure to obtain 822 mg of a colorless liquid (yield 34%).

$^1$H NMR (500 MHz, C$_6$D$_6$, δ/ppm) 3.09 (s, 18H), 1.88 (s, 3H), 1.19 (s, 18H)

$^{13}$C NMR (125 MHz, C$_6$D$_6$, δ/ppm) 177.0, 53.0, 43.0, 32.5, 19.9

Thermal analysis of Zr($^t$BuNC(Me)N$^t$Bu)(NMe$_2$)$_3$

Figure 7:
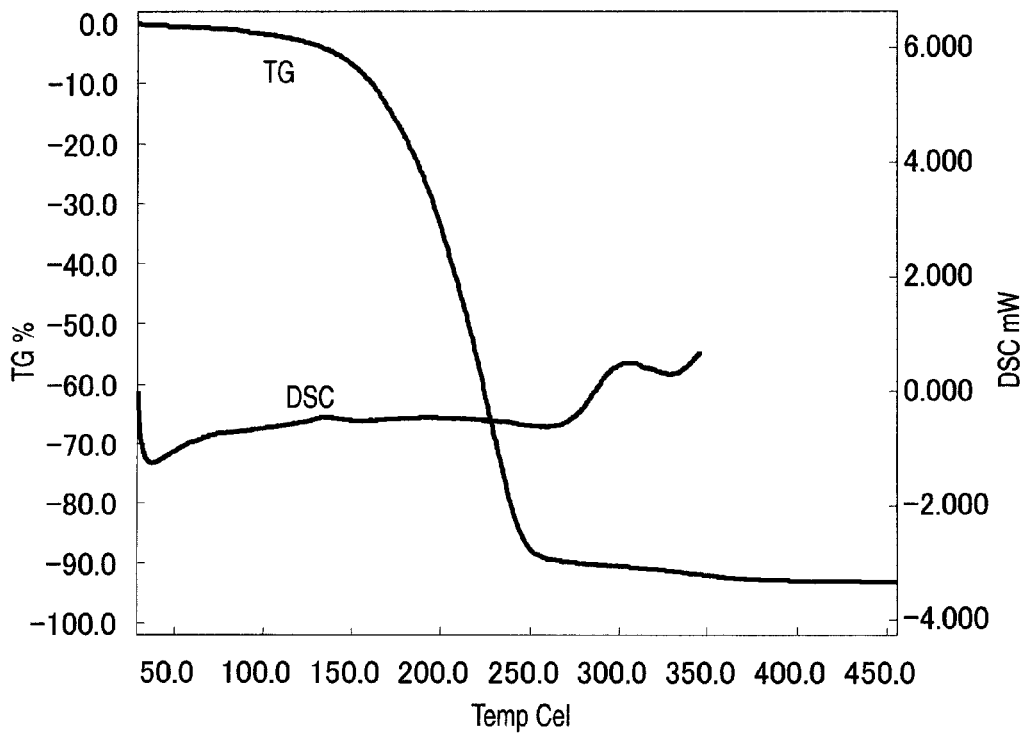
FIG. 7 is the result of TG and DSC measurements of Zr($^t$BuNC(Me)N$^t$Bu)(NMe$_2$)$_3$.

The result of TG (thermogravimetric determination) measured at a temperature rising rate of 10° C./min in an atmosphere which flows argon at 400 ml/min and the result of DSC (differential scanning calorimetry) measured at a temperature rising rate of 10° C./min in a closed vessel were shown in FIG. 7. It was seen from TG to have vaporization properties suitable as a raw material of CVD method or ALD method, and it was seen from DSC that thermal stability is good.

Example 8

Synthesis of (N,N'-diisopropylacetamidinato)tris(ethylmethylamido)zirconium (Zr($^i$PrNC(Me)N$^i$Pr)(NEtMe)$_3$)

In an argon atmosphere, 179 mg (1.26 mmol) of N,N'-diisopropylacetamidine was added to a solution of 401 mg (1.24 mmol) of tetrakis(ethylmethylamido)zirconium dissolved in 5 ml of tetrahydrofuran. After stirring at room temperature for 3 hours, a solvent was distilled away under reduced pressure. A residue obtained was sublimation purified to obtain 332 mg of a colorless solid (yield 66%).

$^1$H NMR (500 MHz, C$_6$D$_6$, δ/ppm) 3.41 (q, J=7 Hz, 6H), 3.35 (sept., J=6 Hz, 2H), 3.06 (s, 9H), 1.51 (s, 3H), 1.26 (t, J=7 Hz, 9H), 1.09 (d, J=6 Hz, 12H)

$^{13}$C NMR (125 MHz, C$_6$D$_6$, δ/ppm) 175.5, 50.0, 48.1, 38.5, 25.4, 15.9, 10.8

Example 9

Synthesis of (N,N'-diisopropylacetamidinato)tris(dimethylamido)hafnium (Hf($^i$PrNC(Me)N$^i$Pr)(NMe$_2$)$_3$)

In an argon atmosphere, 1.81 g (12.7 mmol) of N,N'-diisopropylacetamidine was added to a solution of 4.48 g (12.6 mmol) of tetrakis(dimethylamido)hafnium dissolved in 20 ml of hexane. After stirring at room temperature for 12 hours, a solvent was distilled away under reduced pressure. A residue obtained was distilled under reduced pressure to obtain 4.00 g of a colorless liquid (yield 70%).

$^1$H NMR (500 MHz, C$_6$D$_6$, δ/ppm) 3.45 (sept., J=7 Hz, 2H), 3.15 (s, 18H), 1.49 (s, 3H), 1.05 (d, J=7 Hz, 12H)

$^{13}$C NMR (125 MHz, C$_6$D$_6$, δ/ppm) 175.9, 48.1, 42.8, 25.2, 11.1

Thermal analysis of Hf($^i$PrNC(Me)N$^i$Pr)(NMe$_2$)$_3$

Figure 8:
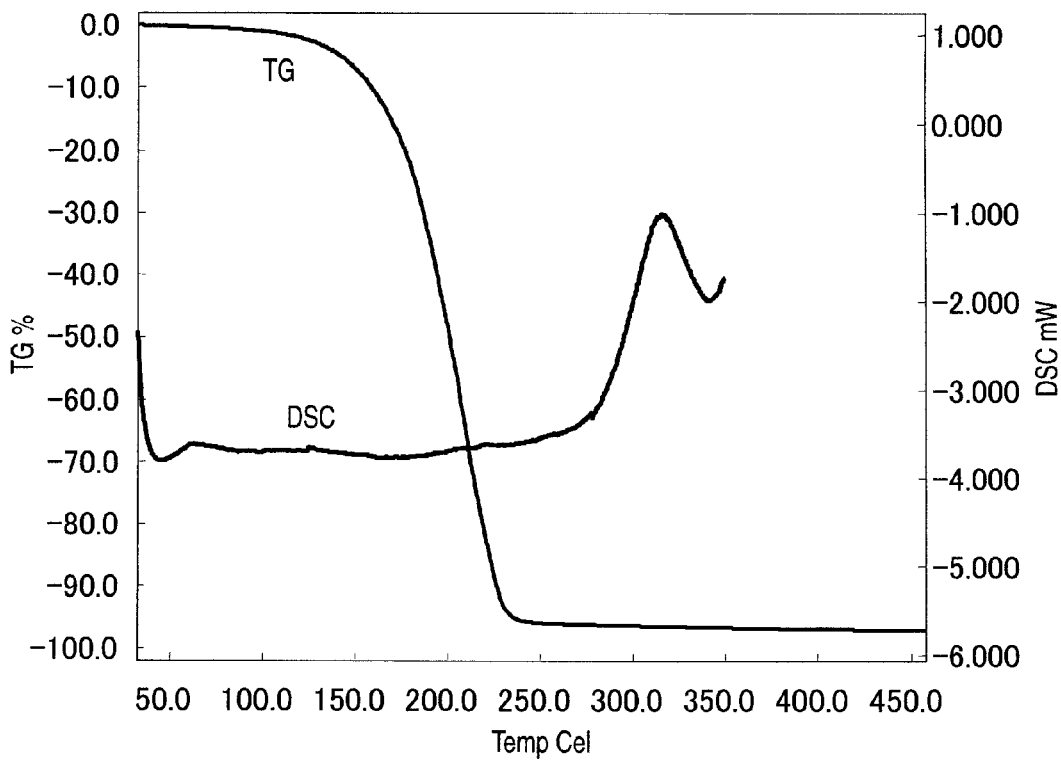
FIG. 8 is the result of TG and DSC measurements of Hf($^i$PrNC(Me)N$^i$Pr) (NMe$_2$)$_3$.

The result of TG (thermogravimetric determination) measured at a temperature rising rate of 10° C./min in an atmosphere which flows argon at 400 ml/min and the result of DSC (differential scanning calorimetry) measured at a temperature rising rate of 10° C./min in a closed vessel were shown in FIG. 8. It was seen from TG to have vaporization properties suitable as a raw material of CVD method or ALD method, and it was seen from DSC that thermal stability is good.

Example 10

Synthesis of (N,N'-diisopropylacetamidinato)tris(dimethylamido)hafnium (Hf($^i$PrNC(Me)N$^i$Pr)(NMe$_2$)$_3$)

In an argon atmosphere, 19.0 g (151 mmol) of N,N'-diisopropylcarbodimide was dissolved in 100 ml of hexane, and 141 ml (151 mmol) of a diethyl ether solution (1.07 mol/l) of methyl lithium was added thereto, followed by stirring at room temperature for 12 hours. A solvent was distilled away under reduced pressure. A white solid obtained was suspended in 150 ml of hexane, and a solution of 53.0 g (149 mmol) of tetrakis(dimethylamido)hafnium dissolved in 20 ml of hexane was added thereto, followed by stirring at 50° C. for 4 hours. After cooling to room temperature, insoluble matters were filtered off using a glass filter, and hexane was distilled away from a filtrate under reduced pressure. A residue obtained was distilled under reduced pressure to obtain 13.6 g of a colorless liquid (yield 20%). As a result of measurement of $^1$H NMR and $^{13}$C NMR in the same manner as in Example 9, the same result as in Example 9 was obtained.

Example 11

Synthesis of (N,N'-diisopropylacetamidinato)tris(dimethylamido)hafnium (Hf($^i$PrNC(Me)N$^i$Pr)(NMe$_2$)$_3$)

In an argon atmosphere, a solution of 211.5 g (596.2 mmol) of tetrakis(dimethylamido)hafnium dissolved in a mixture of 840 ml of tetrahydrofuran and 84 ml of triethylamine was cooled to −20° C., and 85.6 g (43.6 mmol) of N,N'-diisopropylacetamidine was added dropwise thereto. After stirring at room temperature for 4 hours, a solvent was distilled away under reduced pressure. A residue obtained was distilled under reduced pressure to obtain 216.0 g of a pale yellow liquid (yield 80%). As a result of measurement of $^1$H NMR and $^{13}$C NMR in the same manner as in Example 9, the same result as in Example 9 was obtained.

Example 12

Synthesis of (N,N'-diisopropylpropioamidinato)tris(dimethylamido)hafnium (Hf($^i$PrNC(Et)N$^i$Pr)(NMe$_2$)$_3$)

In an argon atmosphere, a solution of 15.5 g (43.7 mmol) of tetrakis(dimethylamido)hafnium dissolved in a mixture of 60 ml of tetrahydrofuran and 6 ml of triethylamine was cooled to −20° C., and 6.84 g (43.8 mmol) of N,N'-diisopropylpropioamidine was added dropwise thereto. After stirring at room temperature for 4 hours, a solvent was distilled away under reduced pressure. A residue obtained was distilled under reduced pressure to obtain 18.1 g of a pale yellow liquid (yield 89%).

$^1$H NMR (500 MHz, C$_6$D$_6$, δ/ppm) 3.52 (sept., J=6 Hz, 2H), 3.17 (s, 18H), 1.97 (q, J=8 Hz, 2H), 1.08 (d, J=7 Hz, 12H), 0.88 (t, J=8 Hz, 3H)

$^{13}$C NMR (125 MHz, C$_6$D$_6$, δ/ppm) 179.9, 47.7, 42.9, 25.5, 18.6, 12.4

Thermal analysis of Hf($^i$PrNC(Et)N$^i$Fr)(NMe$_2$)$_3$

Figure 9:
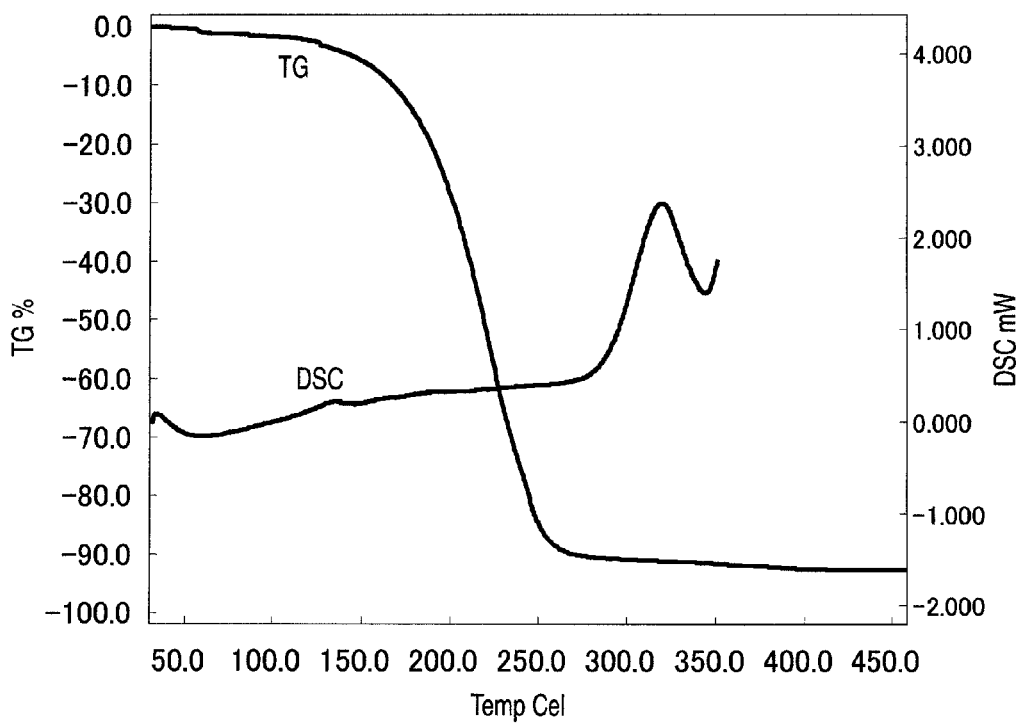
FIG. 9 is the result of TG and DSC measurements of Hf($^i$PrNC(Et)N$^i$Pr)(NMe$_2$)$_3$.

The result of TG (thermogravimetric determination) measured at a temperature rising rate of 10° C./min under argon flow (400 ml/min) and the result of DSC (differential scanning calorimetry) measured at a temperature rising rate of 10° C./min in a closed vessel were shown in FIG. 9. It was seen from TG to have vaporization properties suitable as a raw material of CVD method or ALD method, and it was seen from DSC that thermal stability is good.

Example 13

Synthesis of (N,N'di-tert-butylformamidinato)tris(dimethyl-amido)hafnium (Hf($^t$BuNC(H)N$^t$Bu)(NMe$_2$)$_3$)

In an argon atmosphere, a solution of 11.9 g (33.6 mmol) of tetrakis(dimethylamido)hafnium dissolved in 50 ml of tetrahydrofuran was cooled to −20° C., and 5.25 g (33.6 mmol) of N,N'di-tert-butylformamidine was added dropwise thereto. After stirring at room temperature for 4 hours, a solvent was distilled away under reduced pressure. A residue obtained was distilled under reduced pressure to obtain 11.8 g of pale yellow liquid (yield 75%).

$^1$H NMR (500 MHz, C$_6$D$_6$, δ/ppm) 8.66 (s, 1H), 3.15 (s, 18H), 1.10 (s, 18H)

$^{13}$C NMR (125 MHz, C$_6$D$_6$, δ/ppm) 164.7, 53.6, 42.7, 31.6

Thermal analysis of Hf($^t$BuNC(H)N$^t$Bu)(NMe$_2$)$_3$

Figure 10:
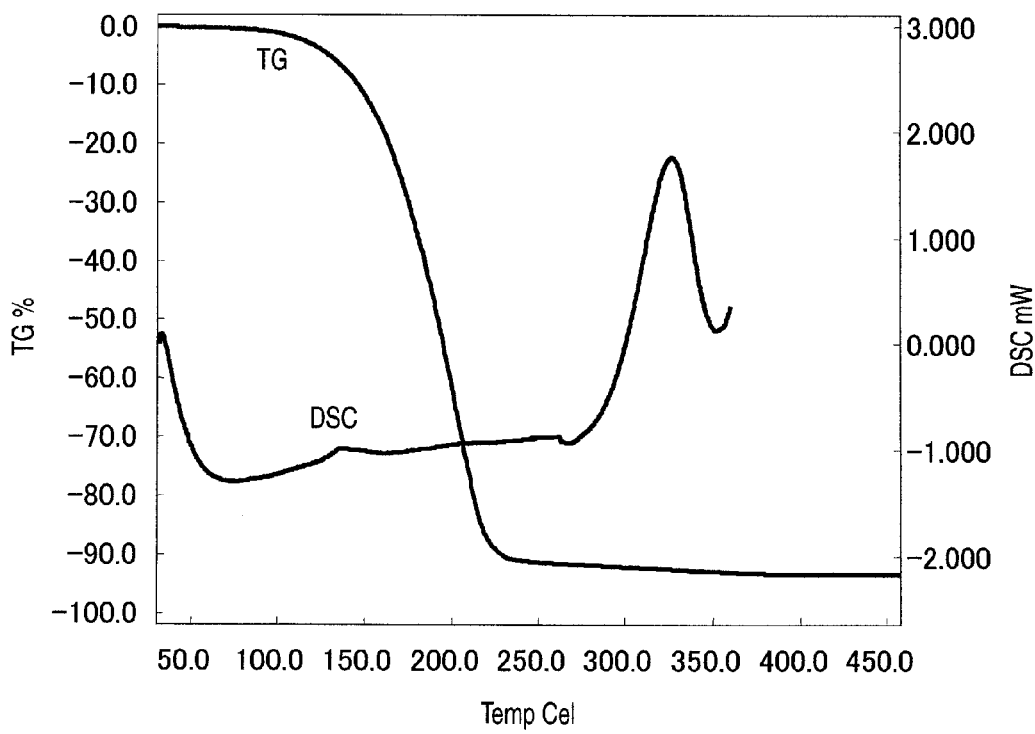
FIG. 10 is the result of TG and DSC measurements of Hf($^t$BuNC(H)N$^t$Bu)(NMe$_2$)$_3$.

The result of TG (thermogravimetric determination) measured at a temperature rising rate of 10° C./min in an atmosphere which flows argon at 400 ml/min and the result of DSC (differential scanning calorimetry) measured at a temperature rising rate of 10° C./min in a closed vessel were shown in FIG. 10. It was seen from TG to have vaporization properties suitable as a raw material of CVD method or ALD method, and it was seen from DSC that thermal stability is good.

Example 14

Synthesis of (N,N'-diisopropylacetamidinato)tris(ethylmethylamido)hafnium (Hf($^i$PrNC(Me)N$^i$Pr)(NEtMe)$_3$)

In an argon atmosphere, 133 mg (0.94 mmol) of N,N'-diisopropylacetamidine was added to a solution of 384 mg (0.93 mmol) of tetrakis(ethylmethylamido)hafnium dissolved in 5 ml of hexane. After stirring at room temperature for hours, a solvent was distilled away under reduced pressure. A residue obtained was distilled under reduced pressure to obtain 173 mg of a colorless liquid (yield 37%).

$^1$H NMR (500 MHz, C$_6$D$_6$, δ/ppm) 3.46 (sept., J=7 Hz, 2H), 3.45 (q, J=7 Hz, 6H), 3.10 (s, 9H), 1.47 (s, 3H), 1.27 (t, J=7 Hz, 9H), 1.09 (d, J=7 Hz, 12H)

$^{13}$C NMR (125 MHz, C$_6$D$_6$, δ/ppm) 175.7, 49.7, 48.0, 38.2, 25.3, 16.1, 11.2

Example 15

Synthesis of (N,N'-diisopropylacetamidinato)tris(ethyl-methylamido)hafnium (Hf($^i$PrNC(Me)N$^i$Pr)(NEtMe)$_3$)

In an argon atmosphere, 140 mg (1.11 mmol) of N,N'-diisopropylcarbodimide was dissolved in 5 ml of hexane, and 1.10 ml (1.08 mmol) of a diethyl ether solution (0.98 mol/l) of methyl lithium was added thereto, followed by stirring at room temperature for 12 hours. A solvent was distilled away under reduced pressure. A white solid obtained was suspended in 5 ml of toluene, and a solution of 446 mg (1.09 mmol) of tetrakis(ethylmethylamido) hafnium dissolved in 5 ml of toluene was added thereto, followed by stirring at 80° C. for 4 hours. After cooling to room temperature, insoluble matters were filtered off using a glass filter, and hexane was distilled away from a filtrate under reduced pressure. A residue obtained was distilled under reduced pressure to obtain 157 mg of a colorless liquid (yield 29%).

Example 16

Synthesis of tris(diethylamido)(N,N'-diisopropylacetamidinato)hafnium (Hf($^i$PrNC(Me)N$^i$Pr)(NEt$_2$)$_3$)

In an argon atmosphere, 105 mg (0.74 mmol) of N,N'-diisopropylacetamidine was added to a solution of 346 mg (0.74 mmol) of tetrakis(diethylamido)hafnium dissolved in 5 ml of hexane. After stirring at room temperature for 12 hours, a solvent was distilled away under reduced pressure. A residue obtained was sublimation purified to obtain 188 mg of a white solid (yield 35%).

$^1$H NMR (500 MHz, C$_6$D$_6$, δ/ppm) 3.48 (q, J=7 Hz, 2H), 3.47 (sept., J=7 Hz, 2H), 1.53 (s, 3H), 1.20 (t, J=7 Hz, 18H), 1.05 (d, J=7 Hz, 12H)

$^{13}$C NMR (125 MHz, C$_6$D$_6$, δ/ppm) 175.7, 48.1, 44.2, 25.4, 16.3, 11.6

Example 17

Synthesis of (N,N'-diisopropylacetamidinato)bis (dimethylamido)aluminum (Al($^i$PrNC(Me)N$^i$Pr) (NMe$_2$)$_2$)

In an argon atmosphere, a solution of 28.1 g (88.2 mmol) of bis(μ-dimethylamido)tetrakis(dimethylamido)-dialuminum dissolved in 100 ml of hexane was cooled to 0° C., and 24.0 g (168.7 mmol) of N,N'-diisopropylacetamidine was added thereto. After stirring at room temperature for 5 hours, a solvent was distilled away under reduced pressure. A residue obtained was distilled under reduced pressure to obtain 32.0 g of a colorless liquid (yield 71%). When this compound was exposed to air, the compound changed to a white solid, but did not combust.

$^1$H NMR (500 MHz, C$_6$D$_6$, δ/ppm) 3.08 (sept., J=6 Hz, 2H), 2.96 (br, s, 12H), 1.24 (s, 3H), 1.00 (d, J=6 Hz, 12H)

$^{13}$C NMR (125 MHz, C$_6$D$_6$, δ/ppm) 174.3, 45.1, 41.3, 25.2, 10.4

Thermal analysis of Al($^i$PrNC(Me)N$^i$Pr)(NMe$_2$)$_2$

Figure 11:
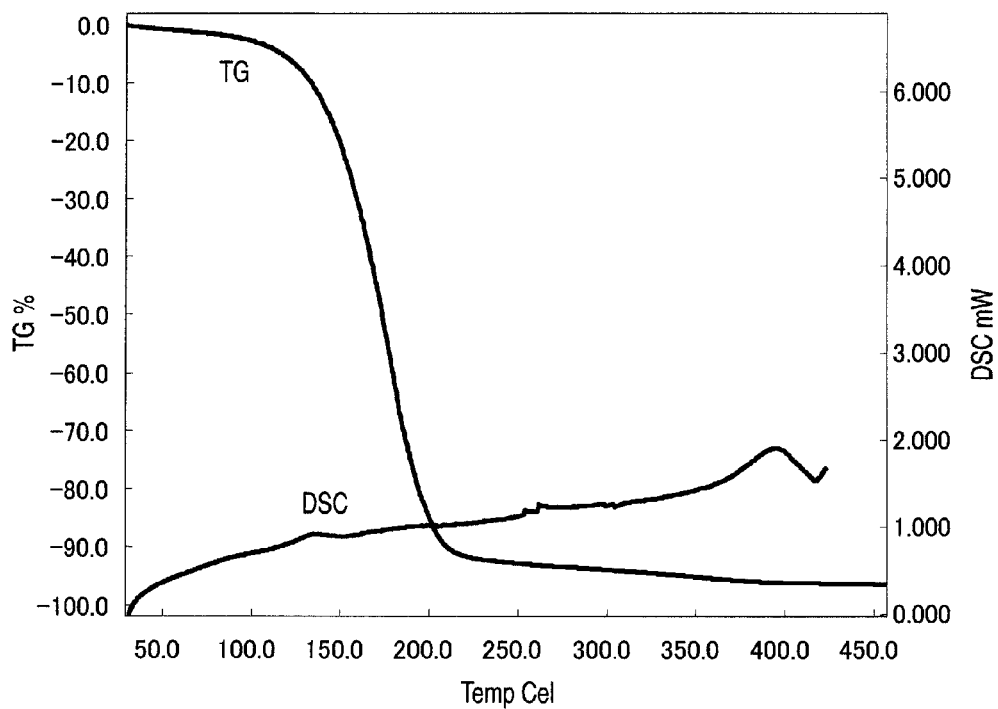
FIG. 11 is the result of TG and DSC measurements of Al($^i$PrNC(Me)N$^i$Pr)(NMe$_2$)$_2$.

The result of TG (thermogravimetric determination) measured at a temperature rising rate of 10° C./min in an atmosphere which flows argon at 400 ml/min and the result of DSC (differential scanning calorimetry) measured at a temperature rising rate of 10° C./min in a closed vessel were shown in FIG. 11. It was seen from TG to have vaporization properties suitable as a raw material of CVD method or ALD method, and it was seen from DSC that thermal stability is good.

Example 18

Synthesis of (N,N'-diisopropylacetamidinato)bis (dimethylamido)gallium (Ga($^i$PrNC(Me)N$^i$Pr) (NMe$_2$)$_2$)

In an argon atmosphere, a solution of 8.78 g (43.5 mmol) of bis(μ-dimethylamido)tetrakis(dimethylamido)-digallium dissolved in 35 ml of hexane was cooled to −20° C., and 6.12 g (43.0 mmol) of N,N'-diisopropylacetamidine was added thereto. After stirring at room temperature for 14 hours, a solvent was distilled away under reduced pressure. A residue obtained was distilled under reduced pressure to obtain 8.21 g of a colorless liquid (yield 74%). When this compound was exposed to air, the compound changed to a white solid, but did not combust.

$^1$H NMR (500 MHz, C$_6$D$_6$, δ/ppm) 3.17 (sept., J=6 Hz, 2H), 3.01 (br, s, 12H), 1.25 (s, 3H), 0.99 (d, J=6 Hz, 12H)

$^{13}$C NMR (125 MHz, C$_6$D$_6$, δ/ppm) 170.2, 45.3, 42.9, 25.4, 10.2

Thermal analysis of Ga($^i$PrNC(Me)N$^i$Pr)(NMe$_2$)$_2$

Figure 12:
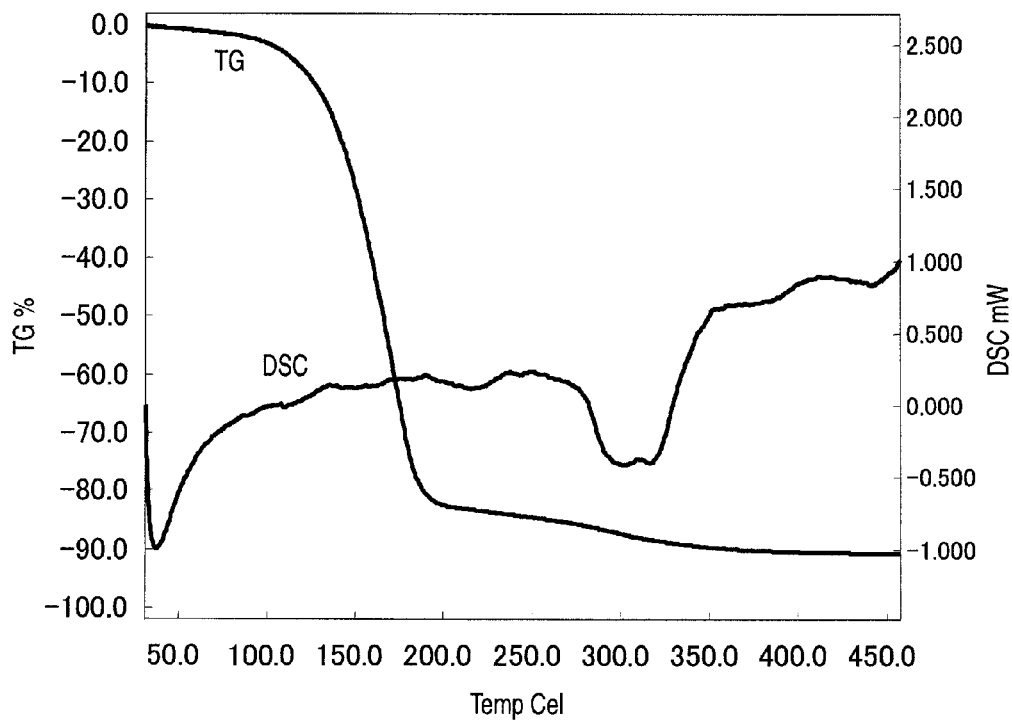
FIG. 12 is the result of TG and DSC measurements of Ga($^i$PrNC(Me)N$^i$Pr)(NMe$_2$)$_2$.

The result of TG (thermogravimetric determination) measured at a temperature rising rate of 10° C./min in an atmosphere which flows argon at 400 ml/min and the result of DSC (differential scanning calorimetry) measured at a temperature rising rate of 10° C./min in a closed vessel were shown in FIG. 12. It was seen from TG to have vaporization properties suitable as a raw material of CVD method or ALD method, and it was seen from DSC that thermal stability is good.

Example 19

Figure 13:
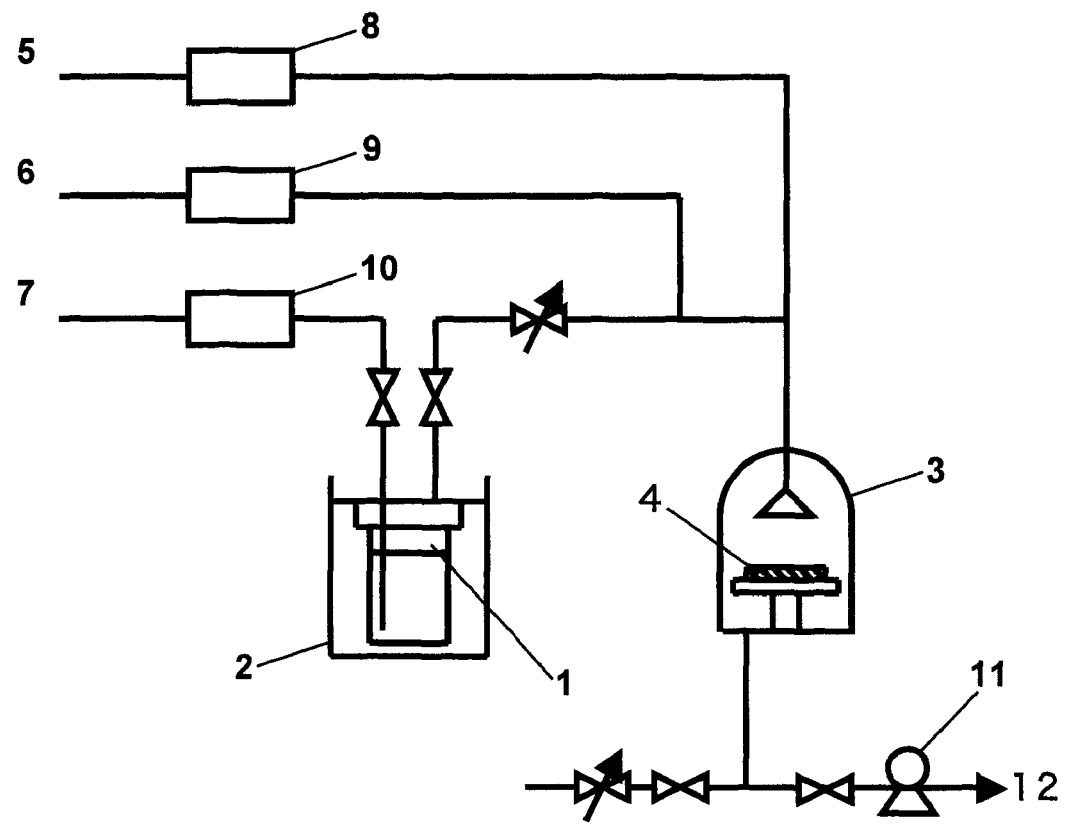
FIG. 13 is a schematic view of a CVD film formation apparatus used in Examples 19 to 24.

Formation of Titanium-Containing Thin Film Using Ti($^i$PrNC(Me)N$^i$Pr) (NMe$_2$)$_3$ Using Ti($^i$PrNC(Me)N$^i$Pr)(NMe$_2$)$_3$ as a raw material, a film was formed on a SiO$_2$/Si substrate under a raw material temperature of 60° C., a carrier gas (Ar) flow rate of 30 sccm, a pressure in a raw material vessel of 100 Torr, a diluent gas (Ar) flow rate of 280 sccm, a reaction gas (O$_2$) flow rate of 90 sccm, a substrate temperature of 400° C. and a pressure in a reaction chamber of 4 Torr using the CVD film formation apparatus shown in FIG. 13 by CVD method over 1 hour. When a film prepared was measured with fluorescent X ray, titanium was detected, and it was confirmed that a titanium-containing film was deposited.

Example 20

Using Ti($^t$BuNC(H)N$^t$Bu)(NMe$_2$)$_3$ as a raw material, a film was formed on a SiO$_2$/Si substrate under a raw material temperature of 50° C., a carrier gas (Ar) flow rate of 30 sccm, a raw material pressure of 100 Torr, a diluent gas (Ar) flow rate of 250 sccm, a reaction gas (O$_2$) flow rate of 120 sccm, a substrate temperature of 400° C. and a pressure in a reaction chamber of 4 Torr using the CVD film formation apparatus shown in FIG. 13 by CVD method over 1 hour. When a film prepared was measured with a fluorescent X ray analyzer, characteristic X ray of Ti was detected, and it was confirmed to be a titanium-containing film. When a film thickness was confirmed by SEM, it was about 110 nm.

Example 21

Formation of Zirconium-Containing Thin Film Using Zr($^i$PrNC(Me)N$^i$Pr)(NMe$_2$)$_3$ Using Zr($^i$PrNC(Me)N$^i$Pr)(NMe$_2$)$_3$ as a raw material, a film was formed using the CVD film formation apparatus shown in FIG. 13 under the condition of the co-presence of oxygen. A film was formed on a SiO$_2$/Si substrate under a raw material temperature of 80° C., a carrier gas (Ar) flow rate of 30 sccm, a raw material pressure of 100 Torr, a diluent gas (Ar) flow rate of 250 sccm, a reaction gas (O$_2$) flow rate of 120 sccm, a substrate temperature of 400° C. and a pressure in a reaction chamber of 4 Torr by CVD method over 1 hour. When a film prepared was measured with a fluorescent X ray analyzer, zirconium was detected, and it was confirmed that a zirconium-containing film was deposited.

Example 22

Formation of Zirconium-Containing Thin Film Using Zr($^t$BuNC(H)N$^t$Bu)(NMe$_2$)$_3$ Using Zr($^t$BuNC(H)N$^t$Bu)(NMe$_2$)$_3$ as a raw material, a film was formed on a SiO$_2$/Si substrate under a raw material temperature of 50° C., a carrier gas (Ar) flow rate of 30 sccm, a raw material pressure of 100 Torr, a diluent gas (Ar) flow rate of 250 sccm, a reaction gas (O$_2$) flow rate of 120 sccm, a substrate temperature of 400° C. and a pressure in a reaction chamber of 4 Torr using the CVD film formation apparatus shown in FIG. 13 by CVD method over 1 hour. When a film prepared was measured with a fluorescent X ray analyzer, characteristic X ray of Zr was detected, and it was confirmed to be a zirconium-containing film. When a film thickness was confirmed by SEM, it was about 150 nm.

Example 23

Formation of Hafnium-Containing Thin Film Using Hf($^i$PrNC(Me)N$^i$Pr)(NMe$_2$)$_3$

Using Hf($^i$PrNC(Me)N$^i$Pr)(NMe$_2$)$_3$ as a raw material, a film was formed on a SiO$_2$/Si substrate under a raw material temperature of 60° C., a carrier gas (Ar) flow rate of 30 sccm, a raw material pressure of 100 Torr, a diluent gas (Ar) flow rate of 350 sccm, a reaction gas (O$_2$) flow rate of 120 sccm, a substrate temperature of 400° C. and a pressure in a reaction chamber of 4 Torr using the CVD film formation apparatus shown in FIG. 13 by CVD method over 1 hour. When a composition of a film prepared was confirmed with X ray diffraction, it was HfO$_2$. When a film thickness was measured with SEM (scanning electron microscope), it was 800 nm.

Example 24

Formation of Aluminum-Containing Thin Film Using Al($^i$PrNC(Me)N$^i$Pr)(NMe$_2$)$_2$

Using Al($^i$PrNC(Me)N$^i$Pr)(NMe$_2$)$_2$ as a raw material, a film was formed on a SiO$_2$/Si substrate under a raw material temperature of 40° C., a carrier gas (Ar) flow rate of 20 sccm, a raw material pressure of 100 Torr, a diluent gas (Ar) flow rate of 220 sccm, a reaction gas (O$_2$) flow rate of 60 sccm, a substrate temperature of 400° C. and a pressure in a reaction chamber of 4 Torr using the CVD film formation apparatus shown in FIG. 13 by CVD method over 1 hour. When a film prepared was measured with a fluorescent X ray analyzer, characteristic X ray of aluminum was detected. When a film composition was confirmed with X ray photoelectron spectroscopy, it was an aluminum oxide film. When a film thickness was confirmed with SEM, it was about 120 nm.

While the invention has been described in detail and with reference to specific embodiments thereof, it will be apparent to one skilled in the art that various changes and modifications can be made therein without departing from the spirit and scope thereof.

This application is based on Japanese Patent Application (Patent Application No. 2005-226886) filed Aug. 4, 2005, Japanese Patent Application (Patent Application No. 2005-326883) filed Nov. 11, 2005, Japanese Patent Application (Patent Application No. 2005-326884) filed Nov. 11, 2005 and Japanese Patent Application (Patent Application No. 2006-192791) filed Jul. 13, 2006, the entire contents thereof being hereby incorporated by reference.

INDUSTRIAL APPLICABILITY

The compound of the present invention has an appropriate thermal stability, an appropriate volatility and an appropriate stability to water and air, and can form a metal-containing thin film by CVD method or ALD method using those. The industrial value of the present invention is remarkable.

The invention claimed is:

1. A compound represented by the general formula (1)

[Chem. 1]

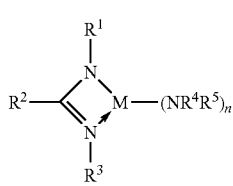

(1)

wherein M represents a Group 4 atom, an aluminum atom, a gallium atom or an indium atom; when M is a Group 4 atom, n is 3, and when M is an aluminum atom, a gallium atom or an indium atom, n is 2; R$^1$ and R$^3$ each independently represent an alkyl group having from 1 to 6 carbon atoms which may be substituted with a fluorine atom, or a trialkylsilyl group represented by R$^6$R$^7$R$^8$Si; R$^6$, R$^7$ and R$^8$ each independently represent an alkyl group having from 1 to 4 carbon atoms; R$^2$ represents a hydrogen atom or an alkyl group having from 1 to 6 carbon atoms which may be substituted with a fluorine atom; R$^2$ and R$^3$ may be combined to form a ring, and R$^4$ and R$^5$ each independently represent an alkyl group having from 1 to 4 carbon atoms which may be substituted with a fluorine atom.

2. The compound as claimed in claim 1, wherein M is a Group 4 atom.

3. The compound as claimed in claim 1, wherein M is an aluminum atom or a gallium atom.

4. The compound as claimed in claim 1, wherein R$^1$ and R$^3$ are an isopropyl group or a tert-butyl group, R$^2$ is a hydrogen atom, a methyl group or an ethyl group, and R$^4$ and R$^5$ are a methyl group or an ethyl group.

5. The compound as claimed in claim 1, wherein M is a titanium atom.

6. The compound as claimed in claim 1, wherein M is a zirconium atom.

7. The compound as claimed in claim 1, wherein M is a hafnium atom.

8. The compound as claimed in claim 1, wherein M is an aluminum atom.

9. A production method of a compound represented by the general formula (1)

[Chem. 4]

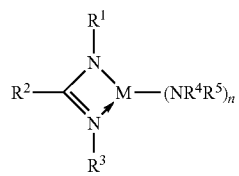

(1)

wherein, M, R$^1$, R$^2$, R$^3$, R$^4$ and R$^5$ are the same as defined below; when M is a Group 4 atom, n is 3; and when M is an aluminum atom, a gallium atom or an indium atom, n is 2, which comprises reacting a compound represented by the general formula (3)

$$M_p(NR^4R^5)_q \qquad (3)$$

wherein M represents a Group 4 atom, an aluminum group, a gallium atom or an indium atom; when M is a Group 4 atom, p is 1 and q is 4; when M is an aluminum atom, a gallium atom or an indium atom, p is 2 and q is 6; and R$^4$ and R$^5$ each independently represent an alkyl group having from 1 to 4 carbon atoms which may be substituted with a fluorine atom with a compound represented by the general formula (2)

[Chem. 2]

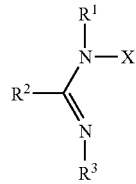

(2)

wherein $R^1$ and $R^3$ each independently represent an alkyl group having from 1 to 6 carbon atoms which may be substituted with a fluorine atom, or a trialkylsilyl group represented by $R^6R^7R^8Si$; $R^6$, $R^7$ and $R^8$ each independently represent an alkyl group having from 1 to 4 carbon atoms; $R^2$ represents a hydrogen atom or an alkyl group having from 1 to 6 carbon atoms which may be substituted with a fluorine atom; $R^2$ and $R^3$ may be combined to form a ring; and X represents a hydrogen atom, a lithium atom or a sodium atom.

10. An M-containing thin film formed by using the compound as claimed in claim 1 as a raw material, wherein M represents a Group 4 atom, an aluminum atom, a gallium atom or an indium atom.

11. A formation method of an M-containing thin film, which comprises using the compound as claimed in claim 1 as a raw material, wherein M represents a Group 4 atom, an aluminum atom, a gallium atom or an indium atom.

* * * * *